United States Patent [19]

Duroux

[11] 4,078,553
[45] Mar. 14, 1978

[54] METHODS FOR INVESTIGATING INTERNAL PHYSIOLOGICAL PHENOMENA

[76] Inventor: Jean Duroux, 12, rue Flatters, 75005 Paris, France

[21] Appl. No.: 726,341

[22] Filed: Sep. 24, 1976

[30] Foreign Application Priority Data

Jun. 14, 1976 France .................................. 76 17995

[51] Int. Cl.² ................................................ A61B 5/04
[52] U.S. Cl. ............................... 128/2.1 Z; 128/2.1 E; 128/DIG. 4
[58] Field of Search ............... 128/2.1 Z, 2.1 E, 2.1 R, 128/1.3, 1.5, 2.06 E, DIG. 4, 404, 417, 418

[56] References Cited

U.S. PATENT DOCUMENTS

| | | | |
|---|---|---|---|
| 2,379,955 | 7/1945 | Eilenberger | 128/2.1 Z |
| 2,590,876 | 4/1952 | Landauer | 128/417 |
| 3,149,627 | 9/1964 | Bagno | 128/2.1 Z |
| 3,340,867 | 9/1967 | Kubicek et al. | 128/2.1 Z X |
| 3,382,434 | 5/1968 | Gibson, Jr. et al. | 128/2.1 Z X |
| 3,387,608 | 6/1968 | Figar | 128/2.06 E |
| 3,789,834 | 2/1974 | Doroux | 128/2.1 Z |
| 3,818,900 | 6/1974 | Nickel | 128/2.1 Z X |
| 3,862,633 | 1/1975 | Allison et al. | 128/2.06 E |
| 3,971,366 | 7/1976 | Motoyama | 128/2.1 Z |

OTHER PUBLICATIONS

Stibitz et al., "A computer-Aided Bridge ... Tissues," Med. & Bio. Eng., Jan. 1974, pp. 100–104.

Primary Examiner—Robert W. Michell
Assistant Examiner—Lee S. Cohen
Attorney, Agent, or Firm—Sughrue, Rothwell, Mion, Zinn and Macpeak

[57] ABSTRACT

The present invention is designed to permit accurate measurement of the variations over the passage of time in the electrical resistivity or in values associated with this resistivity in relation to a defined volume of the body which is acted on by an electromagnetic field.

The electrodes 16 which are designed to pick up the electric field are covered by a thin membrane 15 separating them from the physiological serum 14 contained in a pouch 20 which is applied on the part 21 of the body to be examined.

The invention can be used for any type of investigation of physiological phenomena and for examining all bodies which may contain a plurality of phases.

10 Claims, 8 Drawing Figures

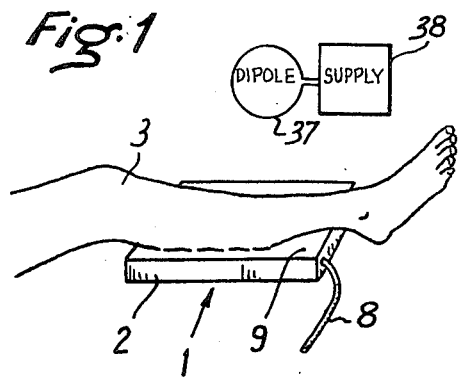
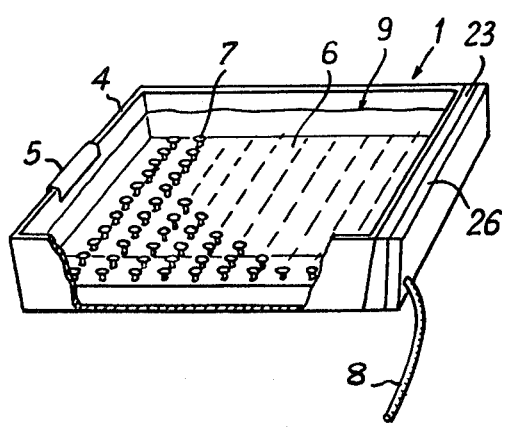
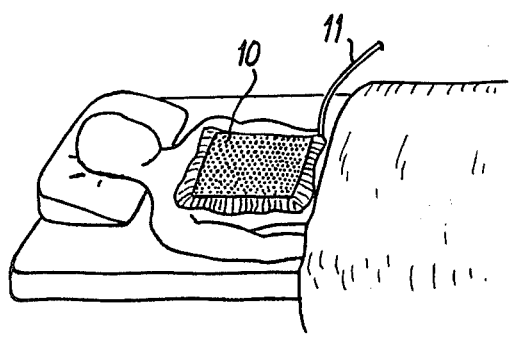
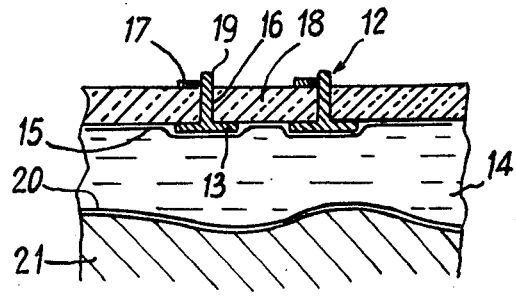

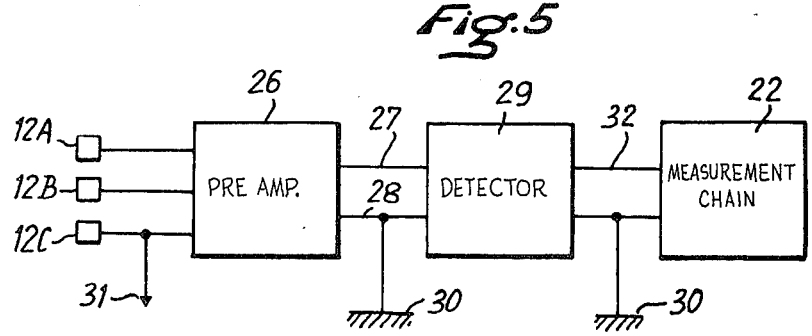
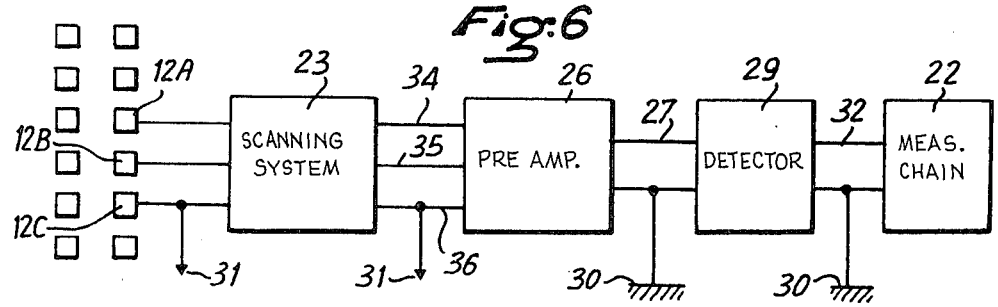
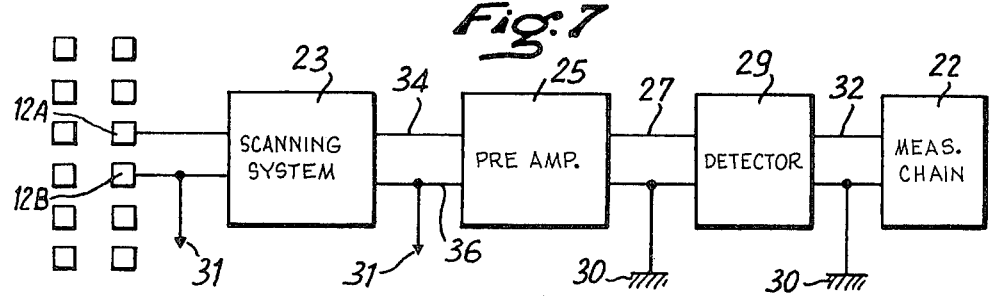
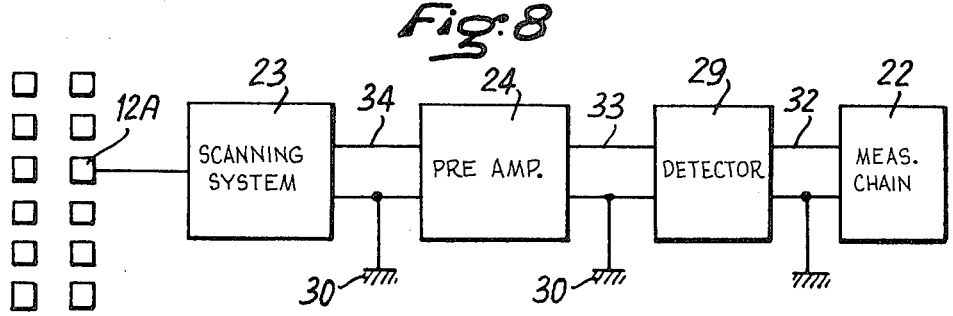

METHODS FOR INVESTIGATING INTERNAL PHYSIOLOGICAL PHENOMENA

BACKGROUND OF THE INVENTION

1. Field of the Invention

The present invention relates to improvements to methods and apparatus as described in French Pat. No. 71.40737, published under No. 2,161,129 (U.S. Pat. No. 3,789,834).

One of the main advantages of the invention described in this patent is that it permits accurate measurement of the variations in time in the electrical resistivity, or in values associated with this resistivity, relating to a defined volume of the body which is acted on by an electromagnetic field of a predetermined frequency.

2. Description of the Prior Art

It frequently happens that physiological phenomena under examination are influenced by other phenomena, even in a well defined area, such that it may be important to determine the simultaneous variations in the resistivities of more limited partial volumes constituting the area to be examined.

There are numerous methods for obtaining internal images of the body, for example, X-ray examination, scintigraphy based on injection of radioactive tracers, ultrasonic echography, thermography, but all of these methods are only effective in specific areas and none of these methods is individually capable of apprehending all of the phenomena under examination.

SUMMARY OF THE INVENTION

The present invention relates to an improvement to the method of investigating physiological phenomena based on impedance variations on the surface of the body, according to the method described in the above patent, characterized in that the source of the electromagnetic field is located so as to make it possible to measure at least one component of the electromagnetic field at a number of points distributed over the surface in question and at which a pick-up is located.

As the physiological phenomena under examination have very low frequencies by comparison with the lowest frequencies employed for emission of the electromagnetic field, it is easy to successively measure the electromagnetic field component or components in all the selected positions before the values thereby obtained have been influenced by physiological rhythms. It is thus possible to avoid the need for a sensor measurement chain while still enabling the image of all parts of the volume to be obtained. Accordingly, it is possible to examine the image obtained from an organ in a given state so as to be able to determine its morphological or pathological anomalies. This examination is effected by observing the cartographical changes over the passage of time as a function of, for example, cardiac or respiratory pulsations or of some other physiological rhythm, or as a function of the excitation to which the patient may be subjected. The examination may also be carried out by following the pathological development of the patient.

Accordingly, the present invention is designed to permit ready investigation of chronic or temporary disorders, such as vascularization problems of the lungs, the cardiac cavities and of major afferent and efferent vessels. It is also designed to permit investigation of pulmonary embolisms and vascular constrictions, diagnosis of periocarditis, detection of pulmonary oedema and examination of the circulation of the brain, detection of cerebral oedema, diagnosis of thromboses, embolisms, splenomegalies, hepatomegalies, etc. The process also enables nephrograms to be readily obtained.

The invention also relates to a process as defined above wherein the electric field without the magnetic field is preferably used as the electromagnetic field component; the source being arranged at a sufficient distance from the volume to be examined so as to produce a field which can be considered constant. The source can be placed on the same side of the body as the measurement device or on the opposite side thereof.

It has been found that the results obtained are excellent and that it is possible to obtain a relatively large number of measurement points by means of electrodes, with contact between the skin and the electrode of only a few square millimeters; the work frequencies employed being sufficiently high to eliminate the high cutaneous resistance which is in the region of 100,000 ohms. Very high quality charts can be produced in this manner.

The invention also relates to a process of this type wherein the electrodes are selected according to the subject under examination; the contact surface between the electrode and the skin increasing according to the corpulence of the subject.

It has been found that it is not only possible to examine the infant or adult human body in this manner but it is also possible to examine very small or very large animals. The invention is obviously also applicable to subjects which are not alive and to all material bodies consisting of one or more solid, liquid or gaseous phases.

The invention also relates to an investigation process as defined above wherein the potential states of the electric field measurement electrodes are recorded at a number of points, either by successively selecting electrodes located at the measurement points, or by scanning at least one pair of electrodes which may or may not be associated with a ground reference electrode.

The invention also relates to a process as defined above wherein irregularities in the surface of the body caused by wrinkles, bony projections, pilosity, moles or other imperfections are controlled by coating the surface of the skin, on which the electrodes are disposed, in a fine layer of physiological serum which is diluted to a greater or lesser extent and which possesses a similar electrical resistivity value to that of the tissues of the bodies under examination. These electrodes can be disposed away from the skin.

In this way, the effect of the irregularities in the skin and accordingly, the slight electrode impedance variations from one measurement point to another, are eliminated.

The invention also relates to a simple apparatus for implementing the above process, wherein the electrodes are supported by a container or pouch holding the serum.

It then suffices to bring the electrodes of the container or compartment—which may be uncovered or enclosed in a thin membrane—into contact with the analysis zone of the patient's body in order to take the resistivity measurements.

The invention also relates to an apparatus for implementing the invention which is characterized in that it comprises at least one electrode switching mechanism and a high frequency preamplifier; selection being effected either by groups of electrodes when ground reference electrodes are provided, or electrode by electrode.

With this apparatus it is equally possible to obtain a diagram of the potential on the surface of the skin or a modulus (E) diagram of the electric field from two potential measurements $Vn$ and $Vn+1$ taken on two consecutive electrodes separated from one another by the length $l$. It is also possible to prepare the diagram from a value which is proportional to the apparent resistivity of the investigated volume by calculating the value $E^2$.

Other objects, features and advantages of the present invention will be made apparent in the course of the following description of an embodiment of the means for implementing the process, and one of its variants, provided by way of non-limitative examples only with reference to the accompanying drawings.

BRIEF DESCRIPTION OF THE DRAWINGS

FIG. 1 is a diagrammatic view of the electrode container during use.

FIG. 2 is a perspective view of the container with a portion removed.

FIG. 3 shows the use of an electrode pouch.

FIG. 4 is a sectional view of the wall of the pouch bearing the electrodes, and

FIGS. 5-8 are diagrammatic views of the circuits of four connection variants of a system of electrodes in a measurement chain.

DESCRIPTION OF THE PREFERRED EMBODIMENT

The container 1 shown in FIGS. 1 and 2 is made of any seal-tight non-conducting material whose rigidity is preferably sufficient to prevent the lateral walls 2 from being crushed by the simple pressure exerted, for example, by the patient's limb 3. If the lateral walls 2 are very rigid, the edges 4 can be covered with a rubber pad 5 which makes it easier to set down the area to be examined.

The base of the container 6 bears an electrode system 7 whose body can be embedded in the non-conducting solid material. Each electrode is electrically connected to a conductor wire; all of these wires being housed, for example, in the sleeve 8, or being connected to a scanning system and preamplifier integral with the container, as will be made apparent when describing FIGS. 5-8.

The container 1 contains a quantity of physiological serum—a simple solution of NaCl in water—sufficient to bathe the surface of the skin and produce a continuous milieu between the electrodes. The electrodes may or may not be protected by a membrane similar to that represented in FIG. 4. In this way, it is possible to eliminate measurement variations caused by skin irregularities such as furrows, wrinkles, moles, pilosity, etc., for the purposes of carrying out a very accurate investigation; the layer of liquid being kept as fine as possible so as to reduce its effect to a negligible quantity. The electrical resistivity of the more or less diluted serum is actually in the same range as that of the human body tissue; the NaCl concentration of the liquid being lower than 9 grams per liter.

If the part of the body to be examined comprises bony projections, for example, which make it impossible to provide a fine liquid layer, the container can be completely filled and the morphology of the volume under investigation and the thickness of the serum layer are then taken into consideration.

If it is not possible to use the container to investigate the area to be examined, a flexible pouch, as shown at 10, can be employed. The electrical cord 11, containing the conductor wires connected to the electrodes, is connected to a single measurement chain 22 (FIGS. 6-8). Each electrode 12A is connected to a scanning system 23 and a preamplifier 24, 25 or 26 rigidly connected to the electrode system. Each of the electrodes 12 (FIG. 4) comprises a part 13 which is isolated from the serum 15 by a fine flexible membrane 15 and a part 16, which can either be connected to an electrical connection 17 embedded in the isolating wall 18 or connected by its end 19 to any conductor disposed outside of the wall 18. At the lower part of the pouch, the part 20 of the fine flexible membrane separates the serum 14 from the part 21 of the patient's body under examination.

According to a variant, the part 15 of the fine flexible membrane can be removed so as to bring the serum into contact with the part 13 of the electrode. Seal-tightness of the serum system is ensured by the perfect seal between the separating wall 18 and the part 16 of the electrodes.

The contact surface of the electrodes can even be reduced to less than 1 mm$^2$ as long as a frequency higher than the 1 -10MHz range is employed.

In investigations which do not require a very delicate diagram, the contact surfaces of the electrodes can have a larger dimension, even in the range of 25 cm$^2$ and larger in the case of examinations carried out on large animals. In this case it is possible to use relatively low frequencies with values lower than a megahertz or even of 100 kHz.

It has been found that the measurement chain 22 for the potentials which are detected at each electrode makes possible accurate measurement of the electrical resistivity variations of each of the parts in the volume under examination. As a result, the spacing between the electrodes for operations requiring knowledge of slight resistivity variations, may be in the range of a centimeter and for high resolution investigations this distance may be reduced to 1 mm.

The connection cords 8 of these electrodes are connected to all the conventional devices for the purpose of selecting any given electrode or group of electrodes according to a predetermined mechanical or electronic scanning operation. The potential measurement of the selected electrode is processed either by direct presentation on a screen or in a computing and recording circuit for determining the electric field, the surface impedance, the electical resistivity or any other parameter proportional to these values relating to the investigated area. This selection, measurement, presentation, computing and recording chain for implementing the process may be of any type comprising, in particular, a television screen and its respective control elements. As this chain, per se, does not form part of the invention, it has only been represented diagrammatically at 22 in FIGS. 5-8. The use of a plurality of frequencies at each measurement point provides investigations at different depths and, by means of suitable computations, produces sections of different depths. Furthermore, whatever type of processing chain 22 is employed for the potentials supplied by the electrodes 12, it will be found that, by using very high source frequencies, it is readily possible to obtain the diagram of the electric field potentials or amplitudes as provided by the network of electrodes much before any physiological rhythm could falsify the measurements. It is thus possible to obtain a visual image of the inner state of the subject virtually at a given instant and it is even possible to obtain an animated visual image by presenting successive images at a cinematographic rate. As a result, it is easy to draw up the diagram of the electric field or even to draw up the plan of the apparent resistivity, to a constant, by calculating the square $E^2$ of the field modulus.

It has been found that excellent results are obtained by arranging the emitting source consisting, for example, of the dipole 37 connected to the supply means 38 (FIG. 1), at a distance of approximately 1 meter from the subject. This distance makes it possible to produce a field of constant value over the entire investigating zone and it can be extended to more than 10 meters.

However, it is obvious that all the investigation methods described in the afore-mentioned parent patent can be employed and that measurement of the electrical field can be accompanied by measurement of a magnetic component.

In view of the extreme ease with which the potential measuring electrodes are selected, the patient can be covered with a type of jacket comprising a more or less dense network of electrodes. Alternatively, if the specific parts of the body to be examined are already known, the corresponding surface can simply be scanned by means of a single row of electrodes which is moved in a given direction.

The electric field component can be measured at a number of points in a specific region, with great accuracy in the case of each point, by means of two adjacent electrodes A and B. This is effected by sampling the potential difference between these electrodes relative to a common ground potential defined by a third electrode C selected in the vicinity of the first two electrodes, as indicated in FIG. 5. In this way, the electric field component E is measured in the direction joining the electrode A to the electrode B. This direction can be selected arbitrarily. In addition, by measuring the components in two rectangular directions in the described manner, it is possible to determine the polarization state of the electric field on the surface of the subject. This provides the advantage of being able to visually indicate with greater contrast the internal resistivity variations of the subject which are at right angles to the direction of the field.

By way of example, FIG. 5 shows a single electric field pick-up consisting of two measuring electrodes 12A and 12B and a ground reference electrode 12C for measuring the potential difference of the electrodes 12A and 12B obtained at the output 27 of a high frequency preamplifier 26. The output 28 is connected to the ground 30 of the measurement chain preceded by the detector 29. Accordingly, it suffices to scan the particular surface area of the subject to be examined by means of this set of three electrodes in the predetermined directions in order to obtain all images as a function of the selected frequencies.

When an electrode network is used, the electrodes can be divided into groups of three, 12A, 12B and 12C (FIG. 6); the electrode 12C constituting the ground reference electrode 31. These electrodes are connected to a manual switching device or electronic scanning device, represented at 23, the outputs 34, 35 and 36 of which are connected to a high frequency differential preamplifier 26. As in the embodiment shown in FIG. 5, the output 27 is connected to the detector 29 and the chain 22. In all cases, the preamplifier 26 and the switch 23 are incorporated in the support means for the electrodes 12 or 7.

According to a variant of the invention, the measurement taken at each point can be simplified by using two electrodes and any type of ground potential.

In this manner, it is possible, as represented in FIG. 7, to use only groups of two electrodes 12A, 12B, with the electrode 12B serving as the ground reference electrode. The outputs of the switching device are transmitted to the high frequency preamplifier 25 and from there to the chain 22 by the detector 29.

According to another variant shown in FIG. 8, it is possible to use only a single electrode 12A for each measurement point, the potential of the electrode being determined relative to the electrical ground 30 of the measuring device; the preamplifier 24 being connected to the detector 29 at 33 as in the preceding cases. However, in this case, it is not possible to determine the polarization state of the electric field although the potentials which are measured do make it possible to directly form a usable image of the inside of the body under examination.

According to another variant, a single potential can be measured at two adjacent points in succession to compute the field components according to the direction determined by the selected points. This is carried out for all the points in a particular region. The field component is thus determined step by step from one electrode to the next.

What is claimed is:

1. A method of investigating physiological phenomena of a portion of a body based on impedance variations on the surface of the body comprising positioning a source of electromagnetic energy relative to the portion of the body, applying an electromagnetic field of substantially constant value from said source over the entire volume of the body portion under examination, providing a plurality of electrodes distributed over the entire surface in question for simultaneous measurement of the values associated with the resistivity of a plurality of points of the surface area under examination and measuring only the electric field component at the points contacted by each of said electrodes to give an instantaneous image of the body portion.

2. A method as set forth in claim 1 further comprising using a plurality of different frequencies for the electromagnetic energy vary the depth of penetration of said electromagnetic energy and obtain measurements for each depth of penetration.

3. A method as set forth in claim 1 wherein said measuring is carried out by successively switching between electrodes to compute and record the field components at each point before a physiological rhythm falsify the diagram of values simultaneously supplied by all of said electrodes.

4. A method as set forth in claim 1 wherein the measuring of the electric field component is carried out by using at each measurement point two adjacent electrodes disposed in any given direction and by measuring the potential difference between these electrodes relative to a common ground potential defined by a third selected electrode disposed in the vicinity of the first two electrodes.

5. A method as set forth in claim 4 wherein the polarization state of the electric field component on the surface of the body is determined by measuring the field component according to two given electrode directions at each measurement point.

6. A method as set forth in claim 1, wherein the measuring of the electric field component is carried out relative to a single ground.

7. A method as set forth in claim 1, wherein the measuring of the electric field component is carried out by using two adjacent electrodes and by measuring the potential difference between these electrodes and successively repeating the operation for adjacent electrodes.

8. A method as set forth in claim 1, wherein said electrodes are disposed in a line and moved in given directions during said measuring.

9. A method as set forth in claim 1, wherein said electrodes are uniformly disposed on the surface area on one side of a support member with electrical connections of the electrodes leading to means for carrying out the measuring being located on the opposite side of the support member.

10. A method as set forth in claim 9, wherein said electrodes are enclosed by a thin flexible membrane sealed to said support member about the edges thereof and containing a serum so as to accommodate uneven body surfaces.

* * * * *

UNITED STATES PATENT AND TRADEMARK OFFICE
CERTIFICATE OF CORRECTION

PATENT NO. : 4,078,553
DATED : March 14, 1978
INVENTOR(S) : Jean DUROUX

It is certified that error appears in the above-identified patent and that said Letters Patent are hereby corrected as shown below:

IN THE CLAIMS:

Col. 6, line 49, after "energy" insert --to--;

Col. 6, line 55, after "rhythm" insert --can--.

Signed and Sealed this

Nineteenth Day of September 1978

[SEAL]

Attest:

RUTH C. MASON
*Attesting Officer*

DONALD W. BANNER
*Commissioner of Patents and Trademarks*